United States Patent [19]

Witt

[11] Patent Number: 4,672,030

[45] Date of Patent: Jun. 9, 1987

[54] TEST KIT FOR THE DETERMINATION OF ACTIVATED THROMBOPLASTIN TIME (PTT) WITH INCREASED SENSITIVITY TO HEPARIN

[76] Inventor: Peter Witt, Vogelwäldeleweg 6, D-7844 Neuenburg, Fed. Rep. of Germany

[21] Appl. No.: 702,284

[22] Filed: Feb. 15, 1985

[30] Foreign Application Priority Data

Feb. 28, 1984 [DE] Fed. Rep. of Germany ....... 3407280

[51] Int. Cl.⁴ .................. C12Q 1/56; G01N 33/86
[52] U.S. Cl. ................................. 435/13; 435/810; 436/69; 436/70
[58] Field of Search .............. 435/13, 810; 436/69, 436/70

[56] References Cited

U.S. PATENT DOCUMENTS 3,179,567  4/1965  Owren ................................ 435/13
3,486,981 12/1969  Speck ................................. 435/13
3,880,714  4/1975  Babson ............................... 435/13

OTHER PUBLICATIONS

Lammle et al., (1983) American Society of Clinical Pathologists, vol. 80, No. 4, pp. 474–477.
Hoffmann et al., (1978) Clinica Chimica Acta, vol. 87, pp. 417–424.
Joist et al., (1977) Journal of Laboratory and Clinical Medicine, vol. 90, No. 6, pp. 1054–1065.

*Primary Examiner*—David M. Naff
*Assistant Examiner*—William J. Herald
*Attorney, Agent, or Firm*—William M. Blackstone

[57] ABSTRACT

Partial thromboplastin time (PTT) is determined for monitoring and controlling heparin therapy with a test kit having increased sensitivity to heparin. Increased sensitivity is obtained by including with reagents in the test kit an organic sulfuric acid or salt thereof such as dodecylbenzenesulfuric acid—sodium salt and/or an organic sulfuric acid ester or salt thereof such as sodium laurylsulfate.

5 Claims, 3 Drawing Figures

TEST KIT FOR THE DETERMINATION OF ACTIVATED THROMBOPLASTIN TIME (PTT) WITH INCREASED SENSITIVITY TO HEPARIN

FIELD OF INVENTION

The invention relates to a test kit for performing a screening test (diagnostic test) for the endogenous coagulation system.

In vivo the endogenous coagulation starts in two simultaneous processes:

The viscous metamorphosis of the blood platelets releases the platelet factor 3. At the same time the contact factor XII is activated by unphysiologic surfaces (collagen, cell fragments) from the damaged vessel. The factors, XIIa, XI, platelet factor 3, and free calcium ions now form the factor-IX-activator. This factor-IX-activator activates factor IX to factor IXa. Factor IXa, together with factor VIII and calcium ions, causes the formation of a factor-X-activator. Consequently, this factor consists of factors IXa, VIII, platelet factor 3, and calcium ions. It activates factor X to factor Xa. Together with factor V, platelet factor III and calcium ions it represents the so-called prothrombin activator which converts factor II (prothrombin) to thrombin.

Thrombin splits off two peptide chains from the fibrinogen molecule and fibrin is formed. By end-to-end and side-to-side accumulations of these fibrin monomers the polymer fibrils are formed, the so-called fibrils. These fibrils are further polymerized by transverse netting to the fibrin, under the influence of the activated factor XIII.

The endogenous coagulation is started in vitro by means of a reagent containing micronized particles to simulate a foreign surface as well as a phospholipid to simulate the platelet factor 3.

The test is described as a determination of the activated partial thromboplastin time, (synonym, PTT-determination). The PTT-determination is mainly performed as a preoperative screening test indicating impairments in the coagulation factors I, II, V, VIII, IX, X, XI, and XII.

The PTT-determination is also performed in connection with monitoring oral anticoagulant therapy which diminishes the activity of factors II, VII, IX, and X. If oral anticoagulant therapy is monitored with another test (the so-called Quick test), factor IX is not covered and remains uncontrolled.

The PTT-determination is also performed to control the therapeutic measures to treat a known coagulation impairment (e.g., classic hemophilia syndrome of hemophilia B syndrome) and to monitor heparin therapy.

This means that a reagent used in the PTT-determination must be sensitive to the factors of the endogenous coagulation system and to heparin.

Equally important is a requirement for good stability of the reconstituted reagent at 37° C., at room temperature, and if stored in a refrigerator.

Performance of the test

The PTT-determination follows the following scheme:

| | |
|---|---|
| Platelet factor reagent (37° C.) | 0.1 ml |
| Patient's plasma (room temperature) | 0.1 ml |
| are mixed and incubated at 37° C. for exactly two minutes | |
| 0.025 M CaCl$_2$ solution (37° C.) | 0.1 ml |
| Determination of time from addition of calcium chloride to start of coagulation (=PTT). | |

This scheme demonstrates that PTT is determined in two steps:

In the first step the plasma factor XII which is sensitive to contact is activated by the addition of the platelet factor reagent which starts the coagulation phase in the endogenous system. The factors participating in the first coagulation are adequately activated after an incubation period of only two minutes.

In the second step calcium chloride solution is added to the formula after the incubation period. The prothrombin conversion factor (complex of factor Xa, factor V, phospholipid, and calcium ions) forming causes the formation of thrombin by which means fibrinogen is converted into fibrin. PTT is measured for the time the calcium ions are added until start of coagulation.

The result of the measurement is stated in seconds.

It is equally possible to indicate the result as a quotient obtained by dividing the PTT of the patient by the PTT of a standard plasma pool.

If instead of the patient plasma a plasma deficient in, e.g., factor VIII or factor IX is used and the result is divided by the PTT of a standard plasma a quotient is obtained which is the higher the more sensitive the reagent used is to a deficit of the respective factor.

BACKGROUND OF THE INVENTION

A test kit to perform PTT determinations is already available in the market providing the necessary reagent in the form of a lyophilized agent which must be reconstituted.

One disadvantage of the commercial test kit for PTT determination is that the sensitivity to heparin still leaves a great deal to be desired so that it is not of much use for the control of heparin therapy.

The object of the present invention is to raise the known PTT test kit's sensitivity, in particular its sensitivity to low-molecular heparin fractions, to a degree also allowing the control of heparin therapy.

SUMMARY OF THE INVENTION

Accordingly, the subject matter of the invention is a test kit for PTT determination by means of a platelet factor reagent, and optionally micronized particles, which is marked by the fact that it contains in addition at least one compound of the formula

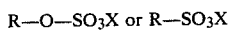

in which R represents a mono or polyunsaturated straight-chained or branched aliphatic or cycloaliphatic hydrocarbon residue, which may be substituted, or an aromatic residue which also may be substituted and X represents a hydrogen atom or a cation.

DETAILED DESCRIPTION

The residue represented by R may stand for an aliphatic or cyclo-aliphatic residue with at least four carbon atoms, e.g., a butyl, isobutyl, tert.-butyl, pentyl, pentenyl, pentadienyl, cyclohexyl, cyclohexenyl, octyl, nonyl, decyl or dodecyl residue or an aromatic residue, e.g., a phenyl, naphthyl, phenanthryl, anthryl, pyridyl, furyl, benzofuryl, isobenzofuryl, thienyl, chinolyl, isochinolyl, phenanthrolinyl, pyrrolyl, pyrimidinyl residue.

In these residues, (R), one or several hydrogen atom(s) may be substituted by, e.g., methyl, ethyl, propyl, octyl, decyl, pentyl, chloropentyl, isopropyl, pententyl, hydroxy, amino, nitro groups or by iodine, chlorine, fluorine, or bromine atoms.

Examples for compounds of the formula R—O—SO$_3$X are: Sodium laurylsulfate, 3,5-dimethylcyclohexanesulfate-Na-salt, isononanesulfate-Na-salt, 5,6-dimethylheptanesulfate-Na-salt, 10-undecenesulfate-Na-salt, undecanesulfate-Na-salt.

Examples for compounds of the formula R—SO$_3$X are: dodecylbenzenesulfonic-acid-Na-salt, pentanesulfonic-acid-Na-salt, naphthaline-4-sulfonic-acid-Na-salt, naphthaline-2,6-disulfonic-acid-Na-salt, 1-naphthol-2-sulfonic-acid-Na-salt, 4-vinyl-benzenesulfonic-acid-Na-salt, 1-octanesulfonic-acid-Na-salt.

The compounds of the formulae R—O—SO$_3$X and R—SO$_3$X may be contained in the reconstituted test solutions in concentrations between 0.05 mmol/l and 100 mmol/l, preferably between 0.2 mmol/l and 20 mmol/l.

The following examples serve to illustrate the invention.

EXAMPLES

The following examples serve to determine the different degrees of sensitivity to heparin of the PTT reagent if dissolved in 3 ml distilled water or in the same quantity of an aqueous solution of pentanesulfonic-acid-Na-salt, dodecylbenzene-sulfonic-acid-Na-salt or sodium-laurylsulfate.

Test 1 is performed with unfractionated heparin, in tests two and three fractionated heparins of relatively low, medium molecular weights are used. The determination is started by the addition of CaCl$_2$.

Figure 1:
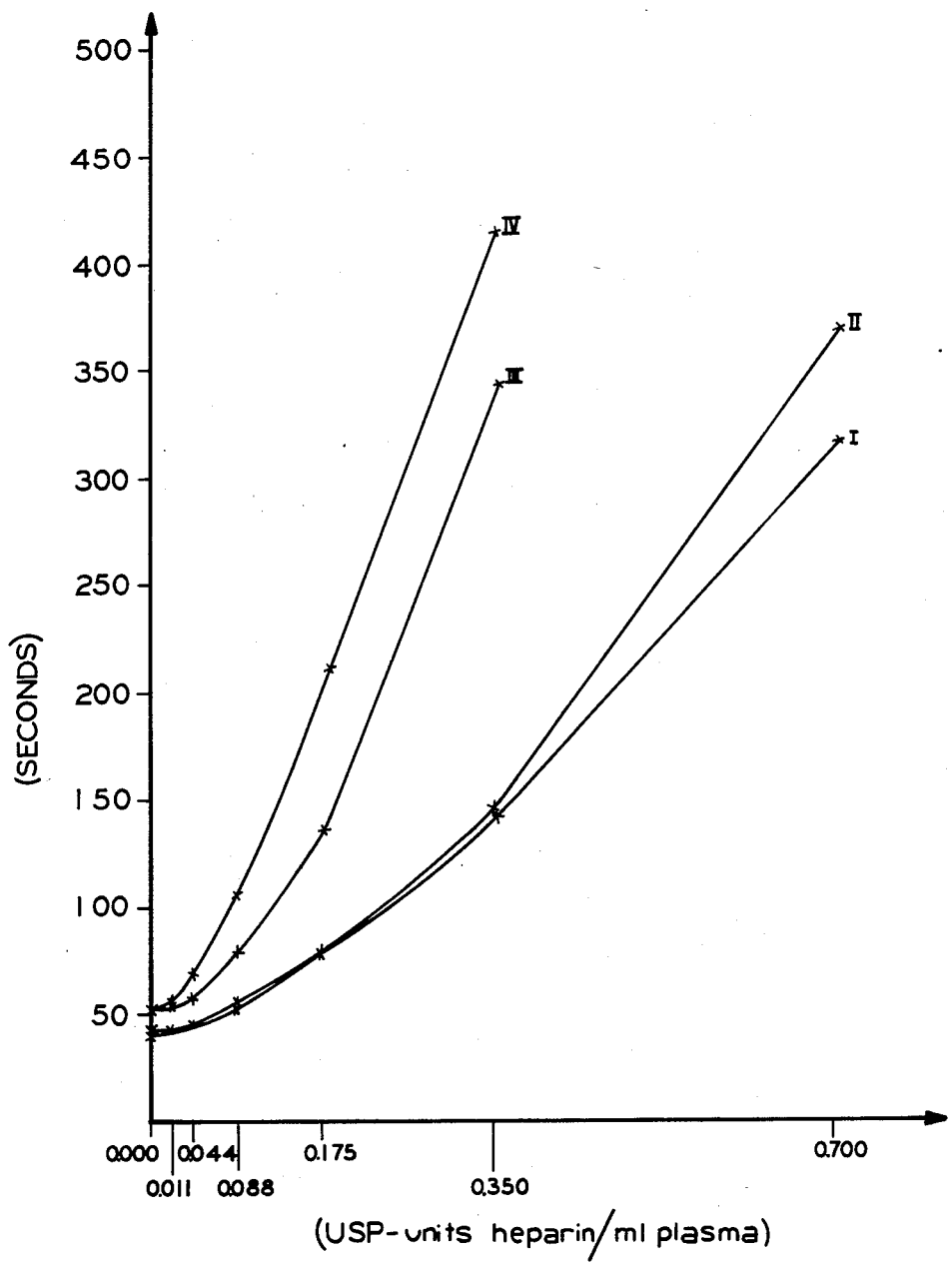
Figure 2:
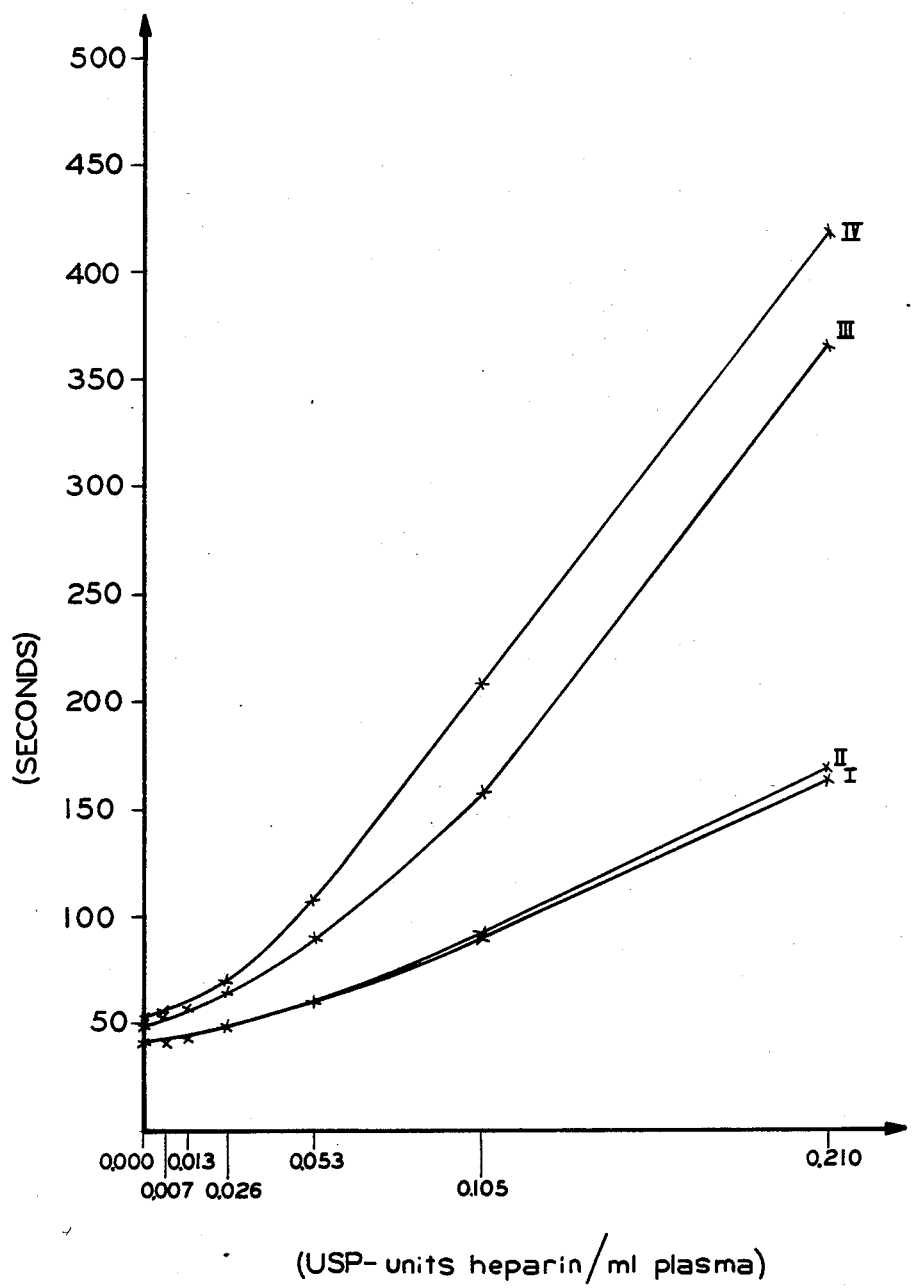
Figure 3:
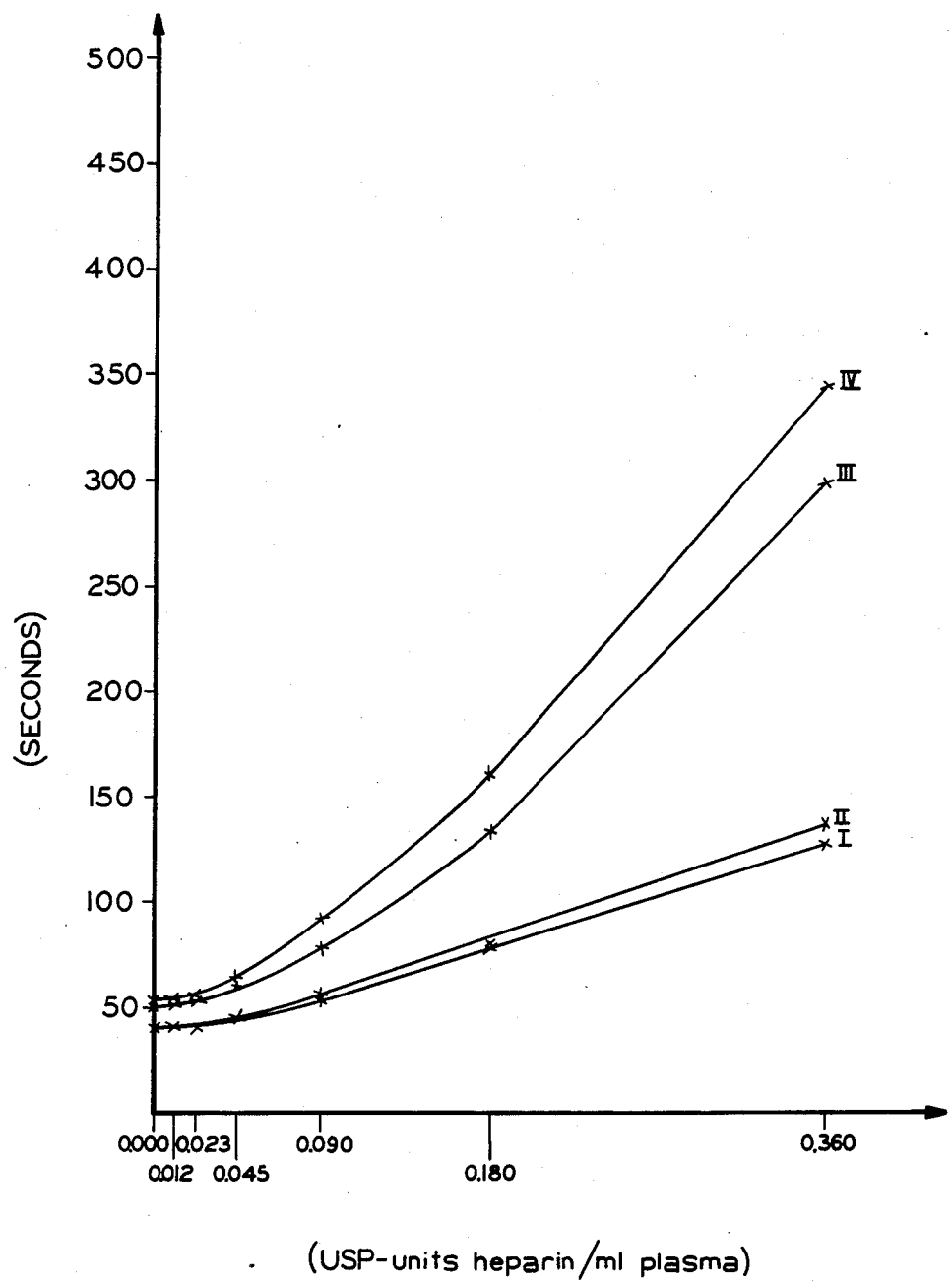

The graphic representation of the results of tests one to three shown in FIGS. 1 to 3 demonstrates that independent of the heparin fractions used the heparin sensitivity is considerably increased by the addition of the additives mentioned.

1. The plasmas used were heparinized with the usual unfractionated heparin from the intestinal mucosa of hogs. The heparin in the plasmas was determined with a commercial test kit and indicated in USP units/ml plasma. FIG. 1 shows the respective coagulation times in seconds plotted against the heparin concentrations in USP units/ml plasma.

2. The plasmas used were heparinized with low-molecular heparin, actually with a commercial mucopolysaccharide of a mean molecular weight of 6000 daltons. FIG. 2 shows the respective coagulation times in seconds plotted against the heparin concentrations in USP-units/ml plasma.

3. The plasmas used were heparinized with a commercial low-molecular heparin of a mean molecular weight of 4040 daltons. FIG. 3 shows the respective coagulation times in seconds plotted against the heparin concentrations in USP-units/ml plasma.

In FIGS. 1–3, the curves are identified as follows:

I. PTT reagent dissolved in distilled water;

II. PTT reagent dissolved in 4.8 mmol/l pentanesulfonic-acid-Na-salt;

III. PTT reagent dissolved in 1.4 mmol/l dodecyclbenzene-sulfonic-acid-Na-salt;

IV. PTT reagent dissolved in 1.1 mmol/l sodium lauryl-sulfate.

What is claimed is:

1. A test kit for the determination of PTT containing test reagents comprising a PTT reagent and, in addition, at least one compound of the formula R—O—SO$_3$X or R—SO$_3$X in which R is a mono or polyunsaturated straight-chained or branched aliphatic or cycloaliphatic hydrocarbon residue, which may be substituted, or an aromatic residue which also may be substituted and X represents a hydrogen atom or a cation.

2. Test kit according to claim 1, wherein the compound of the formula R—O—SO$_3$X or R—SO$_3$X 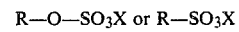 is present in such quantity that 1 liter of a reconstituted solution of the test reagents will contain 0.05 to 100 mmol of said compound.

3. Test kit according to claim 2, wherein the compound of the formula R—O—SO$_3$X or R—SO$_3$X is present in such quantity that 1 liter of a reconstituted solution of the test reagents will contain 0.2 to 20 mmol of said compound.

4. Test kit according to claim 1 wherein said compound is dodecylbenzenesulfonic acid-Na-salt or sodiumlaurylsulfate.

5. Test kit according to claim 1 wherein the compound of the formula R—O—SO$_3$X or R—SO$_3$X is in a reconstituted solution.

* * * * *